(12) United States Patent
Chavan et al.

(10) Patent No.: US 11,931,541 B2
(45) Date of Patent: Mar. 19, 2024

(54) CONNECTOR FOR SELECTIVE OCCLUSION OF DRAINAGE TUBE

(71) Applicant: C. R. Bard, Inc., Franklin Lakes, NJ (US)

(72) Inventors: Varad Chavan, Kolhapur (IN); Rohit Sinha, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 60 days.

(21) Appl. No.: 17/561,458

(22) Filed: Dec. 23, 2021

(65) Prior Publication Data

US 2022/0218974 A1    Jul. 14, 2022

Related U.S. Application Data

(60) Provisional application No. 63/135,447, filed on Jan. 8, 2021.

(51) Int. Cl.
*A61M 39/22* (2006.01)
*A61M 25/00* (2006.01)
(Continued)

(52) U.S. Cl.
CPC ........ *A61M 39/22* (2013.01); *A61M 25/0017* (2013.01); *A61M 39/10* (2013.01);
(Continued)

(58) Field of Classification Search
CPC .. A61M 39/22; A61M 25/0017; A61M 39/10; A61M 2039/0036;
(Continued)

(56) References Cited

U.S. PATENT DOCUMENTS 3,114,916 A    12/1963   Hadley
3,583,401 A    6/1971    Vailiancourt et al.
(Continued)

FOREIGN PATENT DOCUMENTS

EP    1872752 A1    1/2008
EP    2730299 A1    5/2014
(Continued)

OTHER PUBLICATIONS

PCT/US2020/066707 filed Dec. 22, 2020 International Search Report and Written Opinion dated Apr. 15, 2021.
(Continued)

*Primary Examiner* — Nicholas J. Weiss
*Assistant Examiner* — Brandon W. Levy
(74) *Attorney, Agent, or Firm* — Rutan & Tucker LLP

(57) ABSTRACT

A connector for a fluid drainage system having a body defining a drainage lumen extending longitudinally from a distal portion to a proximal portion. The body can include a piston housing and an inlet in fluid communication with a positive air pressure source. A piston is slidably engaged with the piston housing along a transverse axis between a first position and a second position. In the first position, the piston provides fluid communication between the distal portion and the proximal portion of the drainage lumen and occludes fluid communication between the inlet and the drainage lumen. The piston in the second position occludes fluid communication between the distal portion and the proximal portion of the drainage lumen and provides fluid communication between the inlet and the drainage lumen to clear dependent loops, while preventing distal fluid flow into a catheter.

17 Claims, 4 Drawing Sheets

(51) Int. Cl.
*A61M 39/10* (2006.01)
*A61M 39/00* (2006.01)

(52) U.S. Cl.
CPC ............ *A61M 2039/0036* (2013.01); *A61M 2039/226* (2013.01)

(58) Field of Classification Search
CPC .... A61M 2039/226; A61M 2202/0496; A61M 2206/20; A61M 27/00; A61M 39/26; A61M 2039/229; A61M 2039/2493; A61M 39/24; A61M 2005/1403; A61M 1/83; A61M 1/85; A61M 39/223; Y10T 137/86815; Y10T 137/87692; F16K 31/52475; F16K 17/04; F16K 17/046; F16K 17/0473; F16K 17/048; F16K 17/0486; F16K 17/18; F16K 17/196; F16K 31/12; F16K 31/122; F16K 31/1221; F16K 15/025; F16K 15/026; F16K 1/00; F16K 27/02
See application file for complete search history.

(56) References Cited

U.S. PATENT DOCUMENTS

| | | | |
|---|---|---|---|
| 3,598,124 A | 8/1971 | Andersen et al. | |
| 3,661,143 A | 5/1972 | Henkin | |
| 3,861,394 A | 1/1975 | Villari | |
| 3,901,235 A | 8/1975 | Patel et al. | |
| 3,955,574 A | 5/1976 | Rubinstein | |
| 4,084,593 A | 4/1978 | Jarund | |
| 4,265,243 A | 5/1981 | Taylor | |
| 4,305,403 A | 12/1981 | Punn | |
| 4,315,506 A | 2/1982 | Kayser et al. | |
| 4,360,933 A | 11/1982 | Kimura et al. | |
| 4,465,485 A | 8/1984 | Kashmer et al. | |
| 4,531,939 A | 7/1985 | Izumi | |
| 4,631,061 A | 12/1986 | Martin | |
| 4,654,029 A | 3/1987 | D'Antonio | |
| 4,747,166 A | 5/1988 | Kuntz | |
| 4,819,684 A * | 4/1989 | Zaugg | A61M 39/02 137/853 |
| 4,872,579 A | 10/1989 | Palmer | |
| 4,990,137 A | 2/1991 | Graham | |
| 5,002,528 A | 3/1991 | Palestrant | |
| 5,071,411 A | 12/1991 | Hillstead | |
| 5,186,431 A | 2/1993 | Tamari | |
| 5,318,550 A | 6/1994 | Cermak et al. | |
| 5,405,319 A | 4/1995 | Abell et al. | |
| 5,738,656 A | 4/1998 | Wagner et al. | |
| 5,894,608 A | 4/1999 | Birbara | |
| 6,007,521 A | 12/1999 | Bidwell et al. | |
| 6,106,506 A | 8/2000 | Abell et al. | |
| 6,183,454 B1 | 2/2001 | Levine et al. | |
| 6,569,117 B1 * | 5/2003 | Ziv | A61M 39/02 604/246 |
| 8,337,475 B2 | 12/2012 | Christensen et al. | |
| 8,512,301 B2 | 8/2013 | Ma | |
| 10,391,275 B2 | 8/2019 | Burnett et al. | |
| 10,426,919 B2 | 10/2019 | Erbey, II et al. | |
| 10,506,965 B2 | 12/2019 | Cooper et al. | |
| 10,737,057 B1 | 8/2020 | Mikhail et al. | |
| 10,772,998 B2 | 9/2020 | Luxon et al. | |
| 2002/0000253 A1 * | 1/2002 | Fillmore | A61F 5/4405 137/607 |
| 2002/0161317 A1 | 10/2002 | Risk et al. | |
| 2003/0078638 A1 | 4/2003 | Voorhees et al. | |
| 2004/0176746 A1 | 9/2004 | Forral | |
| 2004/0230181 A1 | 11/2004 | Cawood | |
| 2004/0236292 A1 | 11/2004 | Tazoe et al. | |
| 2004/0254547 A1 | 12/2004 | Okabe et al. | |
| 2005/0209585 A1 | 9/2005 | Nord et al. | |
| 2005/0245898 A1 | 11/2005 | Wright et al. | |
| 2005/0261619 A1 | 11/2005 | Gay | |
| 2006/0015190 A1 | 1/2006 | Robertson | |
| 2006/0079854 A1 | 4/2006 | Kay et al. | |
| 2006/0155260 A1 | 7/2006 | Blott et al. | |
| 2006/0235353 A1 | 10/2006 | Gelfand et al. | |
| 2006/0271019 A1 | 11/2006 | Stoller et al. | |
| 2007/0078444 A1 | 4/2007 | Larsson | |
| 2007/0142729 A1 | 6/2007 | Pfeiffer et al. | |
| 2007/0272311 A1 * | 11/2007 | Trocki | A61M 39/223 137/601.2 |
| 2008/0156092 A1 | 7/2008 | Boiarski | |
| 2009/0157016 A1 | 6/2009 | Adahan | |
| 2009/0157040 A1 | 6/2009 | Jacobson et al. | |
| 2009/0326483 A1 | 12/2009 | Green | |
| 2010/0106116 A1 | 4/2010 | Simmons et al. | |
| 2010/0130949 A1 | 5/2010 | Garcia | |
| 2011/0060300 A1 | 3/2011 | Weig et al. | |
| 2012/0323144 A1 | 12/2012 | Coston et al. | |
| 2013/0218106 A1 | 8/2013 | Coston et al. | |
| 2014/0200558 A1 | 7/2014 | McDaniel | |
| 2015/0126975 A1 | 5/2015 | Wuthier | |
| 2015/0290448 A1 | 10/2015 | Pavlik | |
| 2016/0135982 A1 | 5/2016 | Garcia | |
| 2016/0183819 A1 | 6/2016 | Burnett et al. | |
| 2016/0310711 A1 | 10/2016 | Luxon et al. | |
| 2017/0072125 A1 | 3/2017 | Wallenås et al. | |
| 2017/0136209 A1 | 5/2017 | Burnett et al. | |
| 2017/0143566 A1 | 5/2017 | Elku et al. | |
| 2017/0241978 A1 | 8/2017 | Duval | |
| 2017/0312114 A1 | 11/2017 | Glithero | |
| 2018/0015251 A1 | 1/2018 | Lampotang et al. | |
| 2018/0071441 A1 | 3/2018 | Croteau et al. | |
| 2018/0104391 A1 | 4/2018 | Luxon et al. | |
| 2018/0110456 A1 | 4/2018 | Cooper et al. | |
| 2018/0125697 A1 | 5/2018 | Ferrera | |
| 2018/0177458 A1 | 6/2018 | Burnett et al. | |
| 2018/0235523 A1 | 8/2018 | Sauder | |
| 2018/0245699 A1 | 8/2018 | Lee | |
| 2018/0360424 A1 | 12/2018 | Yurek et al. | |
| 2019/0009021 A1 | 1/2019 | Nelson et al. | |
| 2019/0038451 A1 | 2/2019 | Harvie | |
| 2019/0046102 A1 | 2/2019 | Kushnir et al. | |
| 2019/0126006 A1 | 5/2019 | Rehm et al. | |
| 2019/0143094 A1 | 5/2019 | DeMeritt | |
| 2019/0151610 A1 | 5/2019 | Fletter | |
| 2019/0343445 A1 | 11/2019 | Burnett et al. | |
| 2020/0000979 A1 | 1/2020 | Myers | |
| 2020/0061281 A1 | 2/2020 | Desouza et al. | |
| 2020/0315837 A1 | 10/2020 | Radl et al. | |
| 2021/0077007 A1 | 3/2021 | Jouret et al. | |
| 2022/0152345 A1 | 5/2022 | Simiele et al. | |
| 2022/0160949 A1 | 5/2022 | Simiele et al. | |
| 2022/0176031 A1 | 6/2022 | Cheng et al. | |
| 2022/0193366 A1 | 6/2022 | Cheng et al. | |
| 2022/0218890 A1 | 7/2022 | Chavan | |
| 2022/0218973 A1 | 7/2022 | Chavan et al. | |
| 2022/0273213 A1 | 9/2022 | Sokolov et al. | |
| 2022/0305189 A1 | 9/2022 | Chavan et al. | |
| 2022/0330867 A1 | 10/2022 | Conley et al. | |
| 2022/0362080 A1 | 11/2022 | McCorquodale et al. | |
| 2022/0409421 A1 | 12/2022 | Hughett et al. | |
| 2023/0013353 A1 | 1/2023 | Chavan et al. | |
| 2023/0030637 A1 | 2/2023 | Gloeckner et al. | |
| 2023/0054937 A1 | 2/2023 | Chancy et al. | |
| 2023/0083906 A1 | 3/2023 | Jones et al. | |
| 2023/0310837 A1 | 10/2023 | Gamsizlar et al. | |

FOREIGN PATENT DOCUMENTS

| | | |
|---|---|---|
| WO | 2009/026237 A1 | 2/2009 |
| WO | 2012016179 A1 | 2/2012 |
| WO | 2015019056 A1 | 2/2015 |
| WO | 2015/105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2020033752 A1 | 2/2020 |

(56) References Cited

FOREIGN PATENT DOCUMENTS

| WO | 2022/159333 | A1 | 7/2022 |
|---|---|---|---|
| WO | 2022/251425 | A1 | 12/2022 |
| WO | 2023086394 | A1 | 5/2023 |

OTHER PUBLICATIONS

PCT/US2022/012373 filed Jan. 13, 2022 International Search Report and Written Opinion dated Apr. 19, 2022.
PCT/US2022/049418 filed Nov. 9, 2022 International Search Report and Written Opinion dated Feb. 10, 2023.
U.S. Appl. No. 17/526,994, filed Nov. 15, 2021 Restriction Requirement dated Jan. 3, 2023.
U.S. Appl. No. 17/556,942, filed Dec. 20, 2021 Non-Final Office Action dated Jan. 31, 2023.
U.S. Appl. No. 17/561,504, filed Dec. 23, 2021 Non-Final Office Action dated Mar. 14, 2023.
U.S. Appl. No. 17/526,994, filed Nov. 15, 2021 Non-Final Office Action dated May 10, 2023.
U.S. Appl. No. 17/532,454, filed Nov. 22, 2021 Non-Final Office Action dated Mar. 22, 2023.
U.S. Appl. No. 17/542,060, filed Dec. 3, 2021 Non-Final Office Action dated Jun. 27, 2023.
U.S. Appl. No. 17/556,942, filed Dec. 20, 2021 Final Office Action dated Jul. 12, 2023.
U.S. Appl. No. 17/561,504, filed Dec. 23, 2021 Final Office Action dated Jul. 19, 2023.
U.S. Appl. No. 17/863,898, filed Jul. 13, 2022 Non-Final Office Action dated Jul. 17, 2023.
U.S. Appl. No. 17/902,705, filed Sep. 2, 2022 Non-Final Office Action dated May 24, 2023.
U.S. Appl. No. 17/373,568, filed Jul. 12, 2021 Non-Final Office Action dated Nov. 9, 2023.
U.S. Appl. No. 17/526,994, filed Nov. 15, 2021 Final Office Action dated Oct. 24, 2023.
U.S. Appl. No. 17/532,454, filed Nov. 22, 2021 Final Office Action dated Sep. 27, 2023.
U.S. Appl. No. 17/542,060, filed Dec. 3, 2021 Non-Final Office Action dated Nov. 28, 2023.
U.S. Appl. No. 17/556,942, filed Dec. 20, 2021 Non-Final Office Action dated Nov. 3, 2023.
U.S. Appl. No. 17/561,504, filed Dec. 23, 2021 Non-Final Office Action dated Nov. 27, 2023.
U.S. Appl. No. 17/863,898, filed Jul. 13, 2022 Final Office Action dated Nov. 22, 2023.
U.S. Appl. No. 17/902,705, filed Sep. 2, 2022 Non-Final Office Action dated Oct. 19, 2023.
U.S. Appl. No. 17/902,705, filed Sep. 2, 2022 Non-Final Office Action dated Dec. 7, 2023.

* cited by examiner

CONNECTOR FOR SELECTIVE OCCLUSION OF DRAINAGE TUBE

PRIORITY

This application claims the benefit of priority to U.S. Provisional Application No. 63/135,447, filed Jan. 8, 2021, which is incorporated by reference in its entirety into this application.

SUMMARY

Briefly summarized, embodiments disclosed herein are directed to a valved connector for selective occlusion of a drainage lumen to prevent pressure reflux during active clearance of dependent loops within fluid drainage systems.

Fluid drainage systems generally include a flexible drainage tube configured to provide fluid communication with a collection container. Due to the flexibility of the drainage tube, and/or normal patient movements, sections of positive incline can form, where drainage fluid can accumulate, termed "dependent loops." Fluid caught in these dependent loops can lead to various problems. For example, fluid caught in the drainage tube fails to reach the collection container leading to inaccurate fluid output measurements and misdiagnosis of patients or mis-prescribing of drugs. For dependent loops in urine drainage systems, the bladder must push against the pressure of the dependent loop to further excrete urine. This can be uncomfortable for the patient and can lead to injury if the pressure is not alleviated in a timely manner. Further, stagnant fluid within the drainage tube can be a source of pathogens leading to an increased risk of catheter associated urinary tract infections (CAUTI). CAUTI can be highly detrimental to the patient as well as incurring increased costs for additional treatment.

Current practice is for clinicians to manipulate the tubing to urge the fluid caught in the dependent loop towards the collection container. If performed incorrectly, fluid reflux can occur causing infections and complications. Further, there is also an added responsibility on the clinician to perform the manipulation correctly and in a timely manner. Active drainage systems have been developed that introduce a positive air flow to a distal end of the drainage tube to urge fluid through the system to the collection container, clearing these dependent loops. However, the air pressure within the system can cause increased pressure within the patient bladder leading to reflux, increased discomfort and potentially introducing infections to the patient.

Disclosed herein is a connector for a fluid drainage system including, a body defining a drainage lumen extending along a longitudinal axis from a distal portion to a proximal portion, a piston housing including an inlet in fluid communication with a source of pressurized air, a piston slidably engaged with the piston housing along a transverse axis between a first position and a second position. In the first position, the piston provides fluid communication between the distal portion and the proximal portion of the drainage lumen, and occludes fluid communication between the inlet and the proximal portion of the drainage lumen. In the second position, the piston occludes fluid communication between the distal portion and the proximal portion of the drainage lumen, and provides fluid communication between the inlet and the proximal portion of the drainage lumen.

In some embodiments, the piston includes a piston lumen extending along the longitudinal axis and configured to provide fluid communication between the distal portion and the proximal portion of the drainage lumen when the piston is in the first position. In some embodiments, the connector further includes a pneumatic lumen providing fluid communication between the inlet and the proximal portion of the drainage lumen. In some embodiments, the connector further includes a biasing member configured to bias the piston towards the first position. In some embodiments, the connector further includes a distal coupling disposed at a distal end of the body and configured to releasably engage a proximal end of a catheter to provide fluid communication between the catheter and the distal portion of the drainage lumen. The distal coupling is one of a luer slip fit, threaded, spin-nut, interference fit, press-fit, or snap-fit coupling.

In some embodiments the catheter is a Foley catheter configured to drain urine from a bladder of a patient. In some embodiments, the connector further includes a proximal coupling disposed at a proximal end of the body and configured to engage a distal end of a drainage tube, the drainage tube in fluid communication with a collection container. The proximal coupling is one of a luer slip fit, threaded, spin-nut, interference fit, press-fit, or snap-fit coupling. In some embodiments, the connector further includes a guide rail configured to engage a groove to maintain alignment of an axis of the piston channel with the longitudinal axis, the guide rail disposed on one of the piston or an inner surface of the piston housing.

Also disclosed is a method of draining a fluid from a catheter to a collection container including, draining a fluid along a longitudinal axis of a connector, from a distal drainage lumen to a proximal drainage lumen, applying a pressurized fluid to an inlet of the connector, sliding a piston along an axis extending perpendicular to the longitudinal axis from a first position to a second position, occluding fluid flow between the distal drainage lumen and the proximal drainage lumen, and providing fluid communication between the inlet and the proximal drainage lumen.

In some embodiments, the distal drainage lumen is in fluid communication with a lumen of a catheter and the proximal drainage lumen is in fluid communication with a lumen of a drainage tube, the drainage tube coupled to a collection container. The catheter is a Foley catheter. The piston includes a piston lumen extending from a first side to a second side and configured to provide fluid communication between the distal drainage lumen and the proximal drainage lumen when the piston is in the first position. In some embodiments, the method further includes a pneumatic lumen providing fluid communication between the inlet and the proximal drainage lumen. In some embodiments, the method further includes a biasing member configured to bias the piston towards the second position.

In some embodiments, the method further includes a distal coupling disposed at a distal end of the connector and a proximal coupling disposed at a proximal end of the connector. The distal coupling or the proximal coupling is one of a luer slip fit, threaded, spin-nut, interference fit, press-fit, or snap-fit coupling. The piston is disposed within a piston housing of the connector, the piston includes one of a facet, guiderail, or groove configured to engage an inner surface of the piston housing to prevent rotational movement about the axis extending perpendicular to the longitudinal axis.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
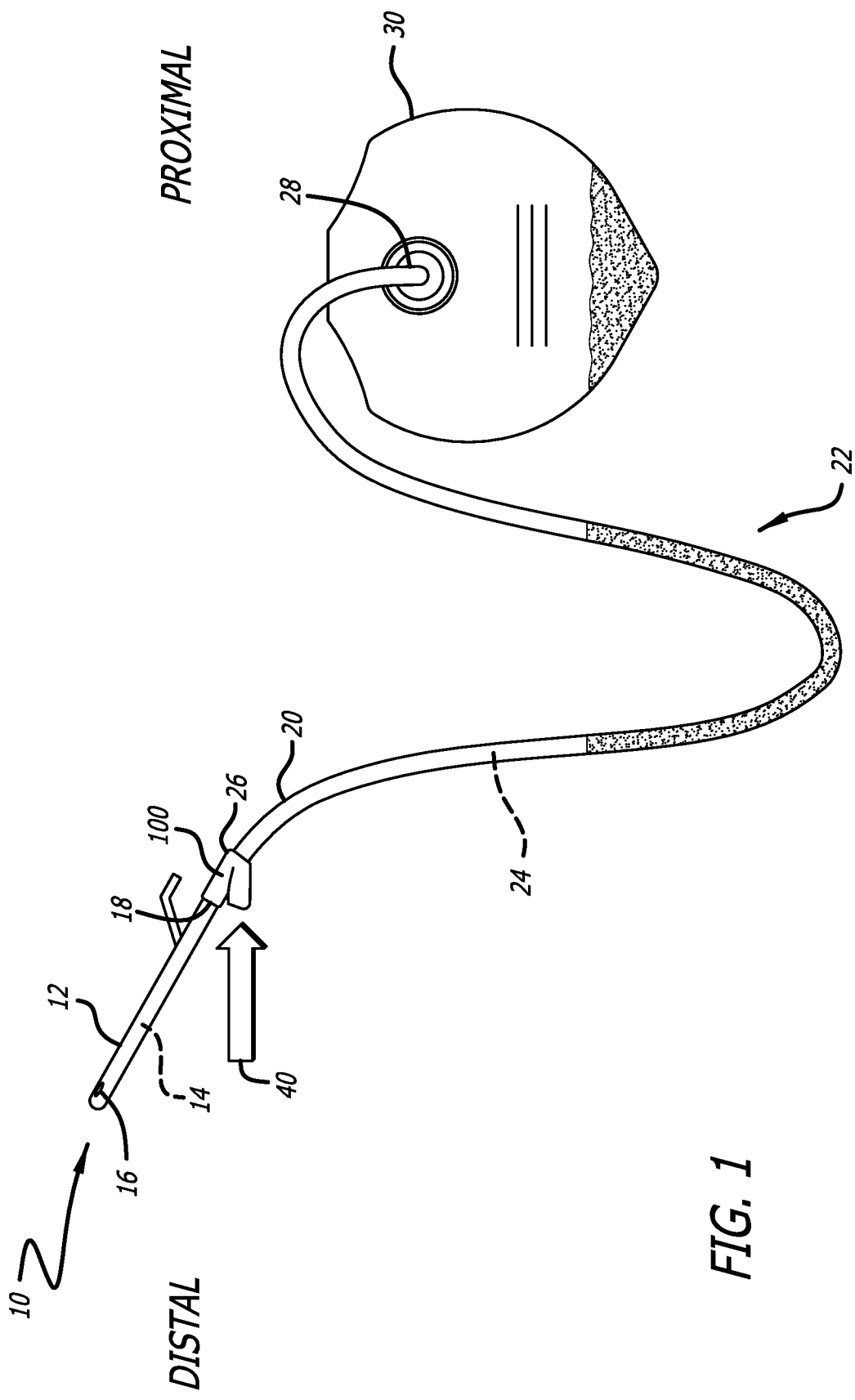
FIG. 1 shows an exemplary fluid drainage system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Figure 2:
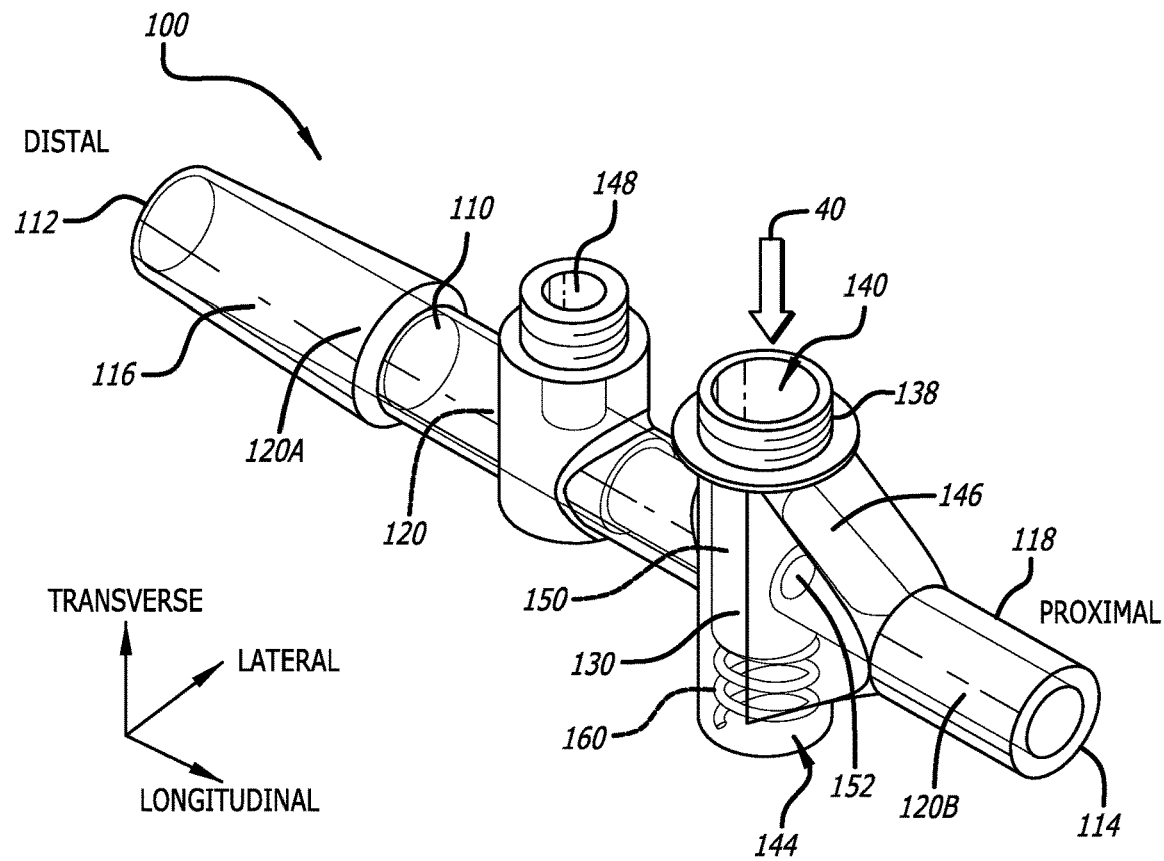
FIG. 2 shows a perspective view of a connector shown in wire frame, in accordance with embodiments disclosed herein.
Figure 3:
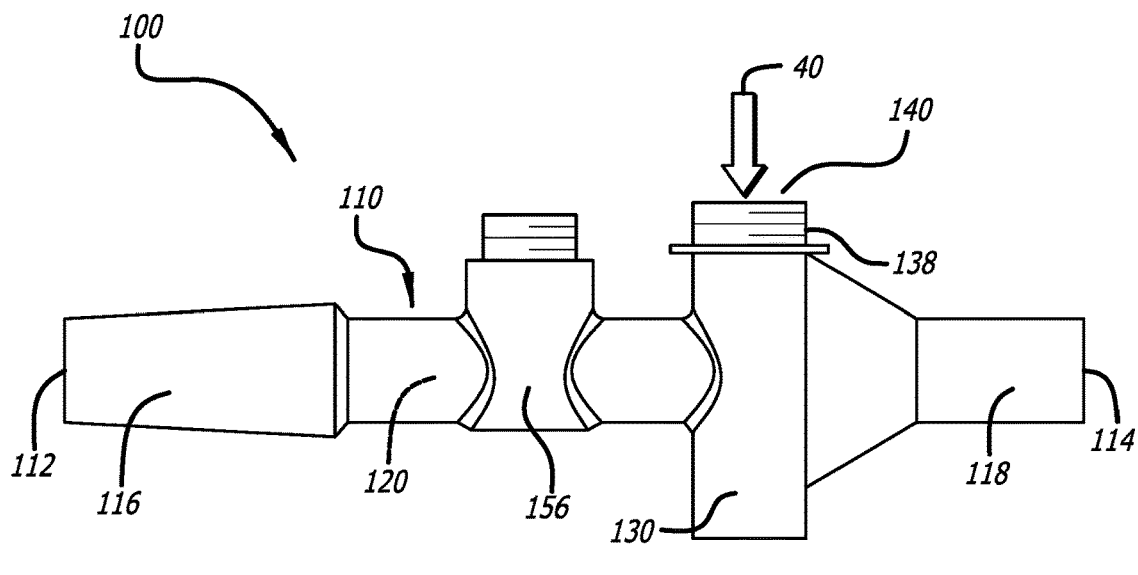
FIG. 3 shows a side view of a connector, in accordance with embodiments disclosed herein.

To assist in the description of embodiments described herein, as shown in FIG. 2, a longitudinal axis extends substantially parallel to an axial length of the drainage lumen. A lateral axis extends normal to the longitudinal axis, and a transverse axis extends normal to both the longitudinal and lateral axes.

As used herein, the term "fluid" can include a gas, liquid, or combination thereof. Unless defined otherwise, all technical and scientific terms used herein have the same meaning as commonly understood by those of ordinary skill in the art.

FIG. 1 shows an exemplary drainage system ("system") 10, configured to drain a fluid from a patient. The system 10 generally includes a catheter 12, a drainage tube ("tube") 20, and a collection container ("container") 30. Exemplary catheters 12 include indwelling catheters, Foley catheters, balloon catheters, peritoneal drainage catheters, or the like, and are configured to be inserted into an orifice within the body of a patient to drain a fluid therefrom. Exemplary fluids can include water, blood, plasma, urine, interstitial fluid, saliva, mucus, pus, or the like. In an embodiment, the catheter 12 can be inserted through the urethra and into a bladder of a patient to drain a fluid, e.g. urine, therefrom. However, it will be appreciated that embodiments disclosed herein can be used with various fluid drainage systems. The catheter 12 includes an eyelet 16 that provides fluid communication with a lumen 14 of the catheter 12, and is configured to drain a fluid, e.g. urine, from a patient.

The drainage tube 20 extends from a distal end 26 to a proximal end 28 to define an axial length, and defines a lumen 24. The distal end 26 of the tube 20 can be in fluid communication with a proximal 18 end of the catheter 12. The proximal end 28 of the tube 20 can be in fluid communication with a collection container 30, to provide fluid communication between the lumen 14 of the catheter 12 and the collection container 30. The tube 20 can be formed of rubber, plastic, polymer, silicone, or similar suitable material. The collection container 30 can include a rigid container, a flexible collection bag, or similar suitable container for receiving a fluid, e.g. urine, drained from the catheter 12.

As shown in FIG. 1, the flexibility of the drainage tube 20 can result in sections of the tube 20 providing a positive incline relative to the direction of fluid flow therethrough. These positive incline portions allow dependent loops 22 to form, which can lead to fluid pooling within the tube 20. The fluid caught within the dependent loop 22 can result in various problems, including acting as a source for CAUTI causing agents and pathogens, inaccurate fluid output measurements, mis-diagnoses of patients, or the like.

In an embodiment, a pump or similar device can introduce a positive air pressure 40 into the tube lumen 24 to urge the residual fluid of the dependent loop 22 through the tube lumen 24 and into the collection container 30. Exemplary pumps can include peristaltic pumps, diaphragm pumps, solenoid pumps, compressors, medical air lines, piston pumps, syringes, bellows, reciprocating pumps, combinations thereof, or the like. Before the positive air pressure 40 is introduced, the lumen 14 of the catheter 12 must be isolated to prevent the positive air pressure 40 flowing distally through the catheter 12 and into the patient, causing discomfort or trauma.

FIGS. 2-7 show various details of an embodiment of a connector piece ("connector") 100 disposed between the catheter 12 and the drainage tube 20, and configured to automatically isolate a fluid path communicating with a catheter 12, when a positive air pressure 40 is applied, to clear dependent loops 22. The connector 100 generally includes a body 110 defining a substantially cylindrical shape extending along a longitudinal axis between from a distal end 112 to a proximal end 114. The body 110 can define a central drainage lumen 120 extending along a longitudinal axis and providing fluid communication between a distal end 112 and a proximal end 114.

The distal end 112 of the body 110 can include a distal coupling 116 configured to releasably engage a proximal end of the catheter 12 and provide fluid communication between the lumen 14 of the catheter 12 and the drainage lumen 120. The proximal end 114 of the body 110 can include a proximal coupling 118 configured to releasably engage a distal end 26 of a drainage tube 20, and provide fluid communication between the drainage lumen 120 of the connector 100 and the lumen 24 of the drainage tube 20. One of the distal coupling 116 or the proximal coupling 118 can include luer slip fit, threaded connector, spin-nut, interference fit, press-fit, snap-fit, or similar connector configured to releasably couple the connector 100 to one of the catheter 12 or the drainage tube 20 with a fluid tight fitting.

In an embodiment, the body 110 further includes a piston housing 130 that defines a substantially cylindrical shaped piston cavity 142 extending along an axis that extends perpendicular to the axis of the drainage lumen 120. In an embodiment the piston cavity 142 extends along a transverse axis, although other axes extending perpendicular to the longitudinal axis are also contemplated. The piston cavity 142 can communicate with the drainage lumen 120. The piston cavity 142 can define a substantially circular cross-sectional shape, however it will be appreciated that other cross-sectional shapes are also contemplated.

The body 110 can further include an inlet 140 configured to provide fluid communication between a pump, or similar source of positive air pressure 40 and the piston cavity 142. The inlet 140 can include a threaded connector 138, or similar connector, configured to couple with a positive air pressure fluid line, or the like. Exemplary positive air pressure fluid lines can include, medical air lines, pumps, syringes, or the like.

In an embodiment, the piston housing 130 can further include a recess 144, communicating with the drainage lumen 120, and extending perpendicular therefrom. The recess 144 can define a substantially circular cross-sectional shape, however it will be appreciated that other cross-sectional shapes are also contemplated. An axis of the piston cavity 142 can align with an axis of the recess 144, disposed opposite the piston cavity 142 across the drainage lumen 120. In an embodiment, the piston cavity 142 can align with the recess 144 along a transverse axis, although it will be appreciate that other axes are contemplated.

In an embodiment, the body 110 can further include a pneumatic lumen 146 that extends between the piston cavity 142 and a proximal portion 120B of the drainage lumen 120 and provides fluid communication therebetween. The pneumatic lumen 146 can extend at an angle of 45° relative to the axis of the drainage lumen 120. However, greater or lesser angles are also contemplated. Advantageously, the angle of the pneumatic lumen 146 can direct the positive air pressure 40 towards the proximal portion 120B of the drainage lumen 120 and into the drainage tube 20, as described in more detail herein.

In an embodiment, the body 110 can further include a sample port 148 communicating with the drainage lumen 120 and extending perpendicular therefrom. In an embodiment, the sample port 148 can include a valve configured to control an access or a fluid flow therethrough. Exemplary valves can include check valves, one way valves, flap valves, duckbilled valves, combinations thereof, or the like. The sample port 148 can be configured to allow a clinician to sample a fluid disposed within the drainage lumen 120. In an embodiment, a pressure sensor can be disposed within the drainage lumen 120 by way of the sample port 148 to detect a fluid pressure disposed within the distal portion 120A of the drainage lumen 120.

Figure 4:
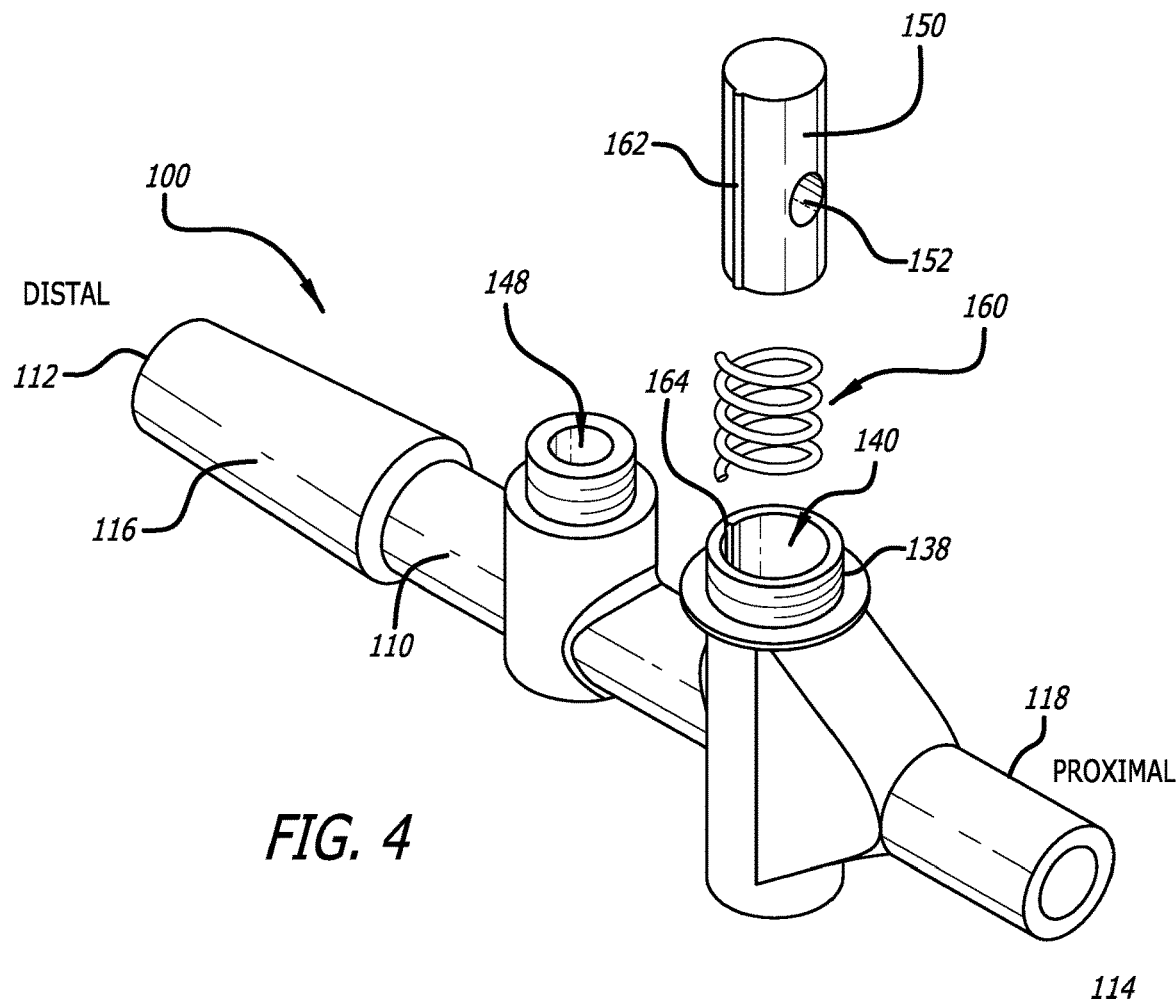
FIG. 4 shows an exploded view of a connector, in accordance with embodiments disclosed herein.
Figure 5:
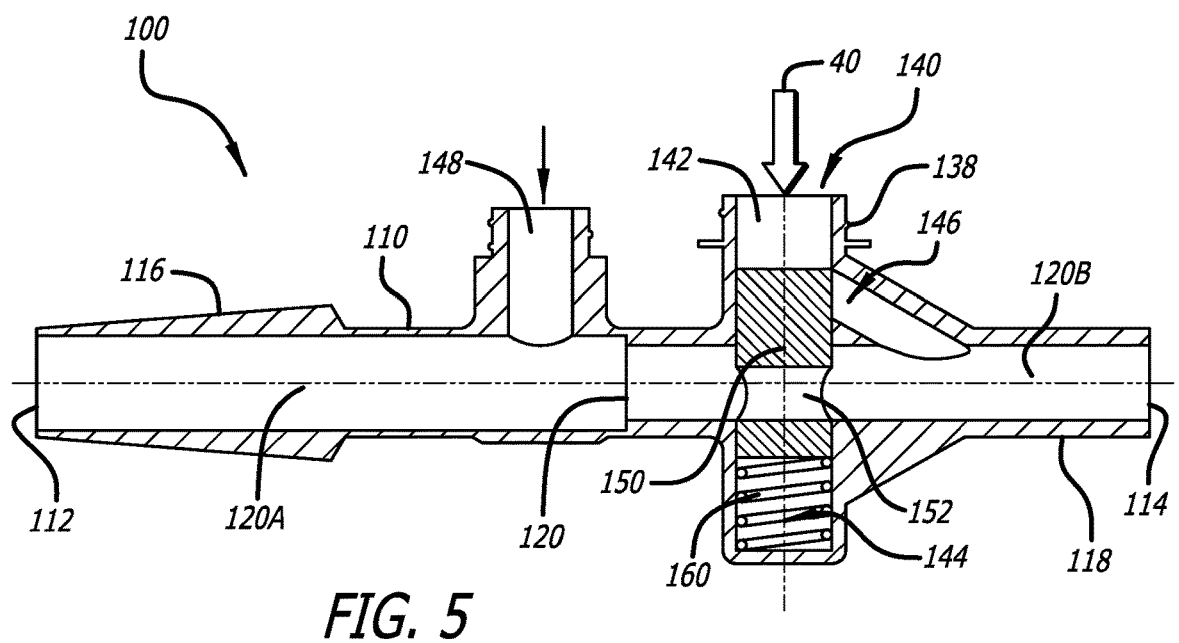
FIG. 5 shows a cross-section view of a connector, in accordance with embodiments disclosed herein.

In an embodiment, as shown for example in FIGS. 2, 4-5, the connector 100 can further include a piston 150. The piston 150 can define a cylindrical shape extending along a length and define a substantially circular cross-sectional shape configured to match an inner cross-sectional shape defined by the piston cavity 142. However, it will be appreciated that other cross-sectional shapes are also contemplated. A diameter of the cross-section of the piston 150 can be the same as, or slightly less than, the diameter of the piston cavity 142 or the recess 144. As such, the piston 150 can be slidably engaged with the piston cavity 142 or the recess 144, of the body 110, along a transverse axis, i.e. an axis that extends perpendicular to the drainage channel 120. The piston 150 can be slidably engaged with the piston cavity 142 and the recess 144 in a fluid tight engagement, as such a fluid cannot pass between an outer surface of the piston 150 and an inner surface of the piston cavity 142 or the recess 144.

Figure 6:
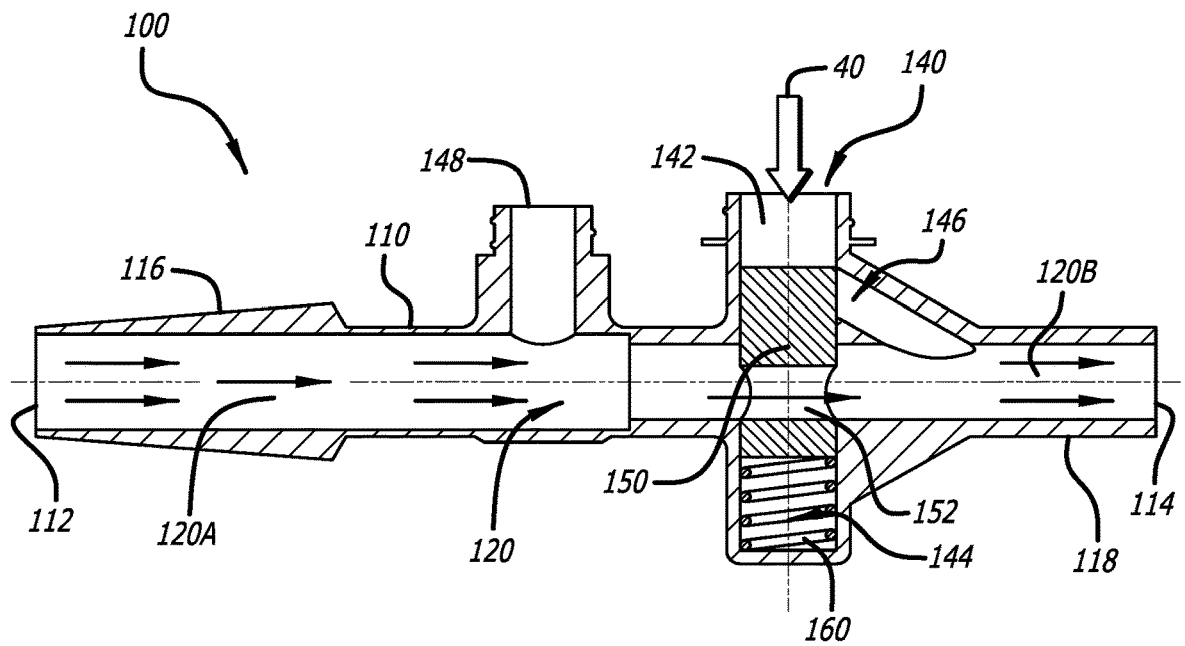
FIG. 6 shows a cross-section view of a connector in a first position, in accordance with embodiments disclosed herein.
Figure 7:
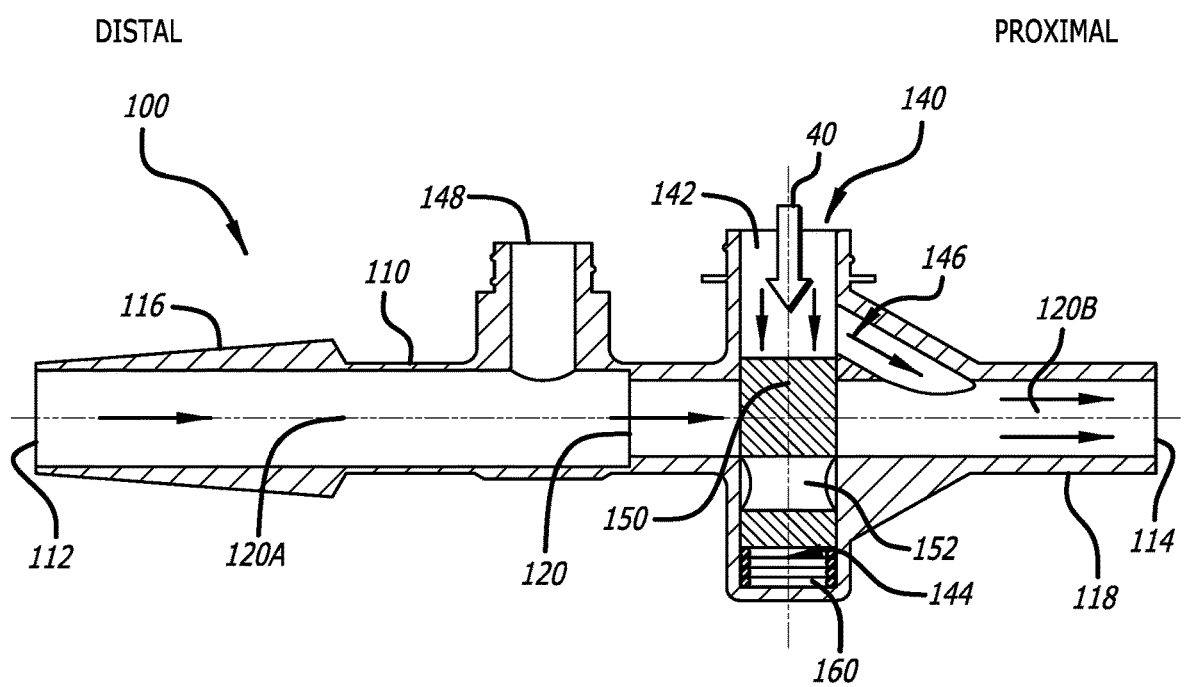
FIG. 7 shows a cross-section view of a connector in a second position, in accordance with embodiments disclosed herein.

In an embodiment, the piston 150 can slide along an axis extending perpendicular to the longitudinal axis, e.g. a transverse axis, between a first position, as shown in FIG. 6 and a second position, as shown in FIG. 7. In the first position, the piston 150 can be configured to allow a fluid flow between a distal portion 120A and a proximal portion 120B of the drainage lumen 120 and to prevent a fluid flow from the inlet 140 from entering the drainage lumen 120. More specifically a portion of the piston can occlude an opening to the pneumatic lumen 146, preventing fluid flow therethrough. In the second position, the piston 150 can be configured to prevent a fluid flow between the distal portion 120A and the proximal portion 120B of the drainage lumen 120, and to allow a fluid flow from the inlet 140 to enter the drainage lumen 120 by way of the pneumatic lumen 146.

In an embodiment, the piston 150 can further include a piston lumen 152 extending through the piston 150 from a first side to a second side, and aligning with an axis of the drainage channel, i.e. substantially with a longitudinal axis. In the first position, the piston lumen 152 can align with the drainage lumen 120 to allow a fluid flow between the distal portion 120A and the proximal portion 120B. In the second position the piston channel 152 can be disposed within the recess 144 and the piston can occlude fluid flow between the distal portion 120A and the proximal portion 120B of the drainage channel 120.

In an embodiment, the connector 100 can include a biasing member 160, for example a compression spring, rubber grommet, or similar biasing member. The biasing member can bias the piston 150 towards the first position (FIG. 6). In an embodiment, an inner surface of the piston cavity 142 or the recess 144 can include one of a facet (not shown), guiderail 162, or groove 164 configured to engage a corresponding facet, guiderail or groove disposed on the piston 150 and designed to allow the piston 150 to slide between the first position and the second position but to prevent rotational movement of the piston 150 within the piston cavity 142, about the transverse axis. Advantageously, this can maintain alignment of the piston lumen 152 with the longitudinal axis.

In an exemplary method of use, a connector 100 can be provided, as described herein. A catheter 12 can be fluidly coupled with a distal coupling 116 and a drainage tube 20 can be fluidly coupled with a proximal coupling 118. A proximal end of the drainage tube 20 can be fluidly coupled with a collection container 30.

The biasing member 160 of the connector 100 can maintain the piston 150 in a first position (FIG. 6) where a fluid can flow freely through the drainage lumen 120. In the first position, the piston lumen 152 aligns with the drainage lumen 120 to allow a fluid to flow therethrough from the catheter 12 at the distal end 112 to the drainage tube 20 at the proximal end 114. Also in the first position, a portion of the piston 150 extends through the piston cavity 142 to occlude the pneumatic lumen 146 that extends between the piston cavity 142 and the proximal portion 120B of the drainage lumen 120.

A user can introduce a pressurized fluid 40 to the connector 100 at the inlet 140. The force of the pressurized fluid 40 can urge the piston 150 from the first position (FIG. 6) to the second position (FIG. 7), compressing the biasing member 160 within the recess 144. In the second position, the piston lumen 152 is disposed within the recess 144 and a portion of the piston 150 occludes the drainage lumen 120. Further, in moving to the second position, the piston 150 moves downward, away from the entrance to the pneumatic lumen 146, allowing the pressurized air 40 to flow from the inlet 140, through the pneumatic lumen 146 and into the proximal portion 120B of the drainage lumen 120. As such, the pressurized fluid 40 can then enter the drainage lumen 24 and urge fluid through the drainage tube 20 and into the container 30, clearing any dependent loops 22. Once the dependent loop 22 is cleared, the pressurized fluid 40 provided at the inlet 140, can be shut off. The reduced pressure acting on the piston 150 allows the biasing member 160 to transition the piston 150 from the second position to the first position. In the first position, the pressurized fluid 40 is prevented from entering the drainage lumen 120 and patency is restored between the distal portion 120A and the proximal portion 120B of the drainage lumen 120.

Advantageously, the piston 150 transitioning between the first position and the second position automatically isolates the catheter lumen 14 from the pressurized fluid 40, preventing any pressurized fluid 40 from entering the catheter lumen 14, causing trauma or discomfort. Further, ceasing the pressurized fluid 40 allows the biasing member 160 to automatically restore patency to the drainage lumen 120, preventing drainage fluid build-up distally of the piston 150. As such, the connector 100 is configured to prevent accidental fluid communication between the pressurized fluid 40 and the catheter lumen 14. Similarly, the connector 100 is configured to re-establish fluid communication between the catheter lumen 14 and the drainage tube 20 when the flow of pressurized fluid 40 is ceased. This prevents accidentally leaving the catheter lumen 14 isolated which would quickly lead to fluid buildup and discomfort for the patient. This is important where the patient is incapacitated and cannot notify nursing staff or where the lack of fluid output may go unnoticed.

Further, the connector 100 does not require any active control inputs to operate the change in fluid flow paths, only requiring the introduction of a positive air pressure 40 to the pneumatic input 140. Advantageously, the connector can be used with various positive air pressure dependent loop clearance systems without requiring any communications coupling therebetween, facilitating automation of the dependent loop clearance systems.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A connector for a fluid drainage system, comprising:
    a body defining a drainage lumen extending along a longitudinal axis from a distal portion to a proximal portion;
    a piston housing providing fluid communication between the distal portion and the proximal portion;
    an inlet configured to provide fluid communication between a source of pressurized air and the piston housing;
    a pneumatic lumen extending external to the piston housing and providing fluid communication between the inlet and the proximal portion of the drainage lumen, a central axis of the pneumatic lumen extending at an angle of between 20° and 70° relative to the longitudinal axis of the drainage lumen; and
    a piston slidably engaged with the piston housing along a transverse axis between a first position and a second position, wherein:
        the piston in the first position provides fluid communication between the distal portion and the proximal portion of the drainage lumen, and occludes an inlet end of the pneumatic lumen to occlude fluid communication between the inlet and the proximal portion of the drainage lumen; and
        the piston in the second position occludes fluid communication between the distal portion and the proximal portion of the drainage lumen, and opens the inlet end of the pneumatic lumen to provide fluid communication between the inlet and the proximal portion of the drainage lumen.

2. The connector according to claim 1, wherein the piston includes a piston lumen extending along the longitudinal axis and providing fluid communication between the distal portion and the proximal portion of the drainage lumen when the piston is in the first position.

3. The connector according to claim 2, further including a guide rail configured to engage a groove to prevent rotation of the piston about the transverse axis and maintain alignment of an axis of the piston lumen with the longitudinal axis, the guide rail disposed on one of the piston or an inner surface of the piston housing.

4. The connector according to claim 1, further including a biasing member configured to bias the piston towards the first position.

5. The connector according to claim 1, further including a distal coupling disposed at a distal end of the body and configured to releasably engage a proximal end of a catheter to provide fluid communication between the catheter and the distal portion of the drainage lumen.

6. The connector according to claim 5, wherein the distal coupling is one of a luer slip fit, threaded, spin-nut, interference fit, press-fit, or snap-fit coupling.

7. The connector according to claim 5, wherein the catheter is a Foley catheter configured to drain urine from a bladder of a patient.

8. The connector according to claim 1, further including a proximal coupling disposed at a proximal end of the body and configured to engage a distal end of a drainage tube, the drainage tube in fluid communication with a collection container.

9. The connector according to claim 8, wherein the proximal coupling is one of a luer slip fit, threaded, spin-nut, interference fit, press-fit, or snap-fit coupling.

10. A method of draining a fluid from a catheter to a collection container, comprising:
draining a fluid along a longitudinal axis of a connector, from a distal drainage lumen through a piston housing to a proximal drainage lumen, the piston housing having an inlet and a piston, the piston slidably engaged with the piston housing between a first position and a second position, the piston in the first position occluding an inlet end of a pneumatic lumen extending between the inlet and the proximal drainage lumen, a central axis of the pneumatic lumen extending at an angle of between 20° and 70° relative to the longitudinal axis of the connector;
applying a pressurized fluid to an inlet of the connector;
sliding the piston along a transverse axis from the first position to the second position;
occluding fluid flow between the distal drainage lumen and the proximal drainage lumen; and
providing fluid communication through the pneumatic lumen between the inlet and the proximal drainage lumen, the pneumatic lumen extending external to the piston housing.

11. The method according to claim 10, wherein the distal drainage lumen is in fluid communication with a lumen of the catheter and the proximal drainage lumen is in fluid communication with a lumen of a drainage tube, the drainage tube coupled to the collection container.

12. The method according to claim 11, wherein the catheter is a Foley catheter.

13. The method according to claim 10, wherein the piston includes a piston lumen extending from a first side to a second side, opposite the first side, and providing fluid communication between the distal drainage lumen and the proximal drainage lumen when the piston is in the first position.

14. The method according to claim 10, further including a biasing member configured to bias the piston towards the first position.

15. The method according to claim 10, further including a distal coupling disposed at a distal end of the connector and a proximal coupling disposed at a proximal end of the connector.

16. The method according to claim 15, wherein the distal coupling or the proximal coupling is one of a luer slip fit, threaded, spin-nut, interference fit, press-fit, or snap-fit coupling.

17. The method according to claim 10, wherein the piston includes one of a facet, a guiderail, or a groove configured to engage an inner surface of the piston housing to prevent rotational movement about the transverse axis.

* * * * *